United States Patent

Carpentier et al.

[19]

[11] Patent Number: 5,888,240
[45] Date of Patent: *Mar. 30, 1999

[54] DISTENSIBLE ANNULOPLASTY RING FOR SURGICAL REMODELLING OF AN ATRIOVENTRICULAR VALVE AND NONSURGICAL METHOD FOR POST-IMPLANTATION DISTENSION THEREOF TO ACCOMODATE PATIENT GROWTH

[75] Inventors: Alexandre C. Carpentier; Alain F. Carpentier, both of Paris, France

[73] Assignee: Baxter International Inc., Deerfield, Ill.

[ * ] Notice: The term of this patent shall not extend beyond the expiration date of Pat. No. 5,593,435.

[21] Appl. No.: 757,693

[22] Filed: Dec. 3, 1996

Related U.S. Application Data

[63] Continuation of Ser. No. 283,059, Jul. 29, 1994, Pat. No. 5,593,435.

[51] Int. Cl.[6] ........................................................ A61F 2/24
[52] U.S. Cl. .................................................................. 623/2
[58] Field of Search ..................................... 623/1, 2, 900; 606/194, 191, 195, 198; 128/898; 600/31

[56] References Cited

U.S. PATENT DOCUMENTS

| | | |
|---|---|---|
| 4,042,979 | 8/1977 | Angell . |
| 4,106,129 | 8/1978 | Carpentier et al. . |
| 4,164,046 | 8/1979 | Cooley . |
| 4,183,102 | 1/1980 | Guiset ........................................ 623/1 |
| 4,290,151 | 9/1981 | Massana . |
| 4,345,340 | 8/1982 | Rosen . |
| 4,489,446 | 12/1984 | Reed . |
| 4,535,483 | 8/1985 | Klawitter et al. . |
| 4,602,911 | 7/1986 | Ahmadi et al. . |
| 4,917,698 | 4/1990 | Carpentier et al. ........................ 623/2 |
| 5,061,277 | 10/1991 | Carpentier et al. . |
| 5,064,431 | 11/1991 | Gilbertson et al. . |
| 5,071,431 | 12/1991 | Sauter et al. . |
| 5,163,953 | 11/1992 | Vine . |
| 5,201,880 | 4/1993 | Wright et al. . |
| 5,258,021 | 11/1993 | Duran ..................................... 623/900 |
| 5,306,296 | 4/1994 | Wright et al. . |
| 5,593,424 | 1/1997 | Northrup . |
| 5,593,435 | 1/1997 | Carpentier et al. ........................ 623/2 |
| 5,607,471 | 3/1997 | Seguin et al. . |
| 5,628,790 | 5/1997 | Davidson et al. . |
| 5,716,397 | 2/1998 | Myers . |

FOREIGN PATENT DOCUMENTS

| | | |
|---|---|---|
| 0-338-994 | 10/1989 | European Pat. Off. . |
| 2306671 | 4/1975 | France . |
| 3230858 | 8/1982 | Germany . |
| 197710 | 10/1977 | Russian Federation . |
| WO 91/17721 | 11/1991 | WIPO . |
| WO 97/19655 | 6/1997 | WIPO . |

*Primary Examiner*—Robert A. Clarke
*Attorney, Agent, or Firm*—Guy L. Cumberbatch

[57] ABSTRACT

The distensible annuloplasty ring which may be enlarged, in situ, by application of dilatory pressure by way of a balloon or other dilating apparatus. The distensible annuloplasty ring of the invention is usable in pediatric patients whose growth, subsequent to surgical implantation of the ring, will necessitate subsequent enlargement of the ring to accommodate growth of the annulus. The invention includes a transluminal and/or transeptal method for post-implantation enlargement of the annuloplasty ring via catheter.

13 Claims, 4 Drawing Sheets

DISTENSIBLE ANNULOPLASTY RING FOR SURGICAL REMODELLING OF AN ATRIOVENTRICULAR VALVE AND NONSURGICAL METHOD FOR POST-IMPLANTATION DISTENSION THEREOF TO ACCOMODATE PATIENT GROWTH

This is a continuation of Ser. No. 283,059 now U.S. Pat. No. 5,593,435, filed Jul. 29, 1994, issued Jan. 14, 1997.

FIELD OF THE INVENTION

The present invention relates generally to medical devices, and more particularly to annuloplasty ring useable for surgical correction of certain disorders of the atrioventricular (i.e., mitral and tricuspid) valves of the human heart.

BACKGROUND OF THE INVENTION

In many patients who suffer from disfunction of the mitral and/of tricuspid valve(s) of the heart, surgical repair of the valve (i.e. "valvuloplasty") is a desirable alternative to valve replacement. One specific group of patients who are typically candidates for such surgery are children who suffer from congenital atrioventricular septal defect (AVSD).

Remodelling of the valve annulus (i.e. "annuloplasty") is central to many reconstructive valvuloplasty procedures. Such remodelling of the valve annulus may be accomplished by implantation of a prosthetic ring (i.e. "annuloplasty ring") to stabilize the annulus and to correct or prevent valvular insufficiency which may result from defect or disfunction of the valve annulus.

The prior art has included numerous annuloplasty rings, such as those described in U.S. Pat. Nos. 4,042,979 (Angell); 4,290,151 (Massana); 4,898,446 (Reed); 4,602,911 (Ahmadi et al.); 5,061,277 (Carpentier et al.); and 5,201,880 (Wright et al.), as well as International Patent Publication WO 91/17721 and Foreign Patent Publication SU197710.

One problem associated with the annuloplasty rings of the prior art is that, when such annuloplasty rings are implanted into children (such as pediatric patients with AVSD) the subsequent growth of the patient may render the annuloplasty ring too small for its intended function. Thus, follow-up surgery my be necessary to replace the originally implanted annuloplasty ring with a larger ring suitable for the then-current size of the patient.

Although some of the annuloplasty rings of the prior art have incorporated means for adjusting the size of the ring at the time of implantation, applicant is aware of no prior art annuloplasty ring which is constructed and equipped for post-implantation size adjustment, in situ, to accommodate changes in annular size due to growth of the patient.

SUMMARY OF THE INVENTION

The present invention provides a distensible annuloplasty ring which may be expanded, in situ, by way of a transvascularly and/or transeptally positionable valve expansion apparatus.

In accordance with a presently preferred embodiment of the invention, the annuloplasty ring may be made up of a plurality of separate segments or leaves which are slidably or movably secured to one another to form a ring having the desired configuration of the mitral or tricuspid valve annulus. When dilatory or outward pressure is exerted against the inner surface of the ring, as may be accomplished by way of a radially expandable member (e.g., a balloon or expandable wire cage) introduced within the annulus of the remodeled valve, such pressure will cause the segments or leaves to slide or distend relative to one another. Such sliding or distention of the segments or leaves will expand the ring to a larger annular size.

It is preferable that the individual segments or leaves which form the ring incorporate locator lugs and notches, or other suitable registry apparatus or frictional locator apparatus, for controlling the amount of distension which results from each application of dilatory pressure, and for preventing the segments or leaves from inadvertently slipping or moving relative to one another.

The ring may he covered by a stretchable or distensible sheath to prevent blood from entering into and/or stagnating in the spaces between the articulating surfaces of the individual segments or leaves. Also, a stretchable or distensible suture ring, formed of needle-penetrable material such as Dacron mesh, is mounted on the ring to facilitate suturing-in-place of the ring at the time of implantation.

In accordance with an alternative embodiment of the invention, the annuloplasty ring may be formed of a non-elastic polymer or other distensible material which will remain distended after the application of outward dilatory pressure has been terminated.

Still further in accordance with the invention, there is provided a method for performing remodelling annuloplasty of an atrioventricular valve, with a subsequent transluminal and/or transeptal procedure for enlargement of the a annuloplasty ring to accommodate growth of the patient.

Further objects and advantages of the invention will become apparent to those skilled in the art, upon reading of the following Detailed Description of the Preferred Embodiments and consideration of the accompanying drawings.

BRIEF DESCRIPTION OF THE DRAWINGS

FIG. 3a is an enlarged, cut away perspective view, of a portion of the annuloplasty ring of FIG. 3.

DETAILED DESCRIPTION OF THE PREFERRED EMBODIMENT

The following detailed description and the accompanying drawings are intended to describe and show certain presently preferred embodiments of the invention only, and are not intended to limit the spirit or scope of the invention in any way.

Figure 1:
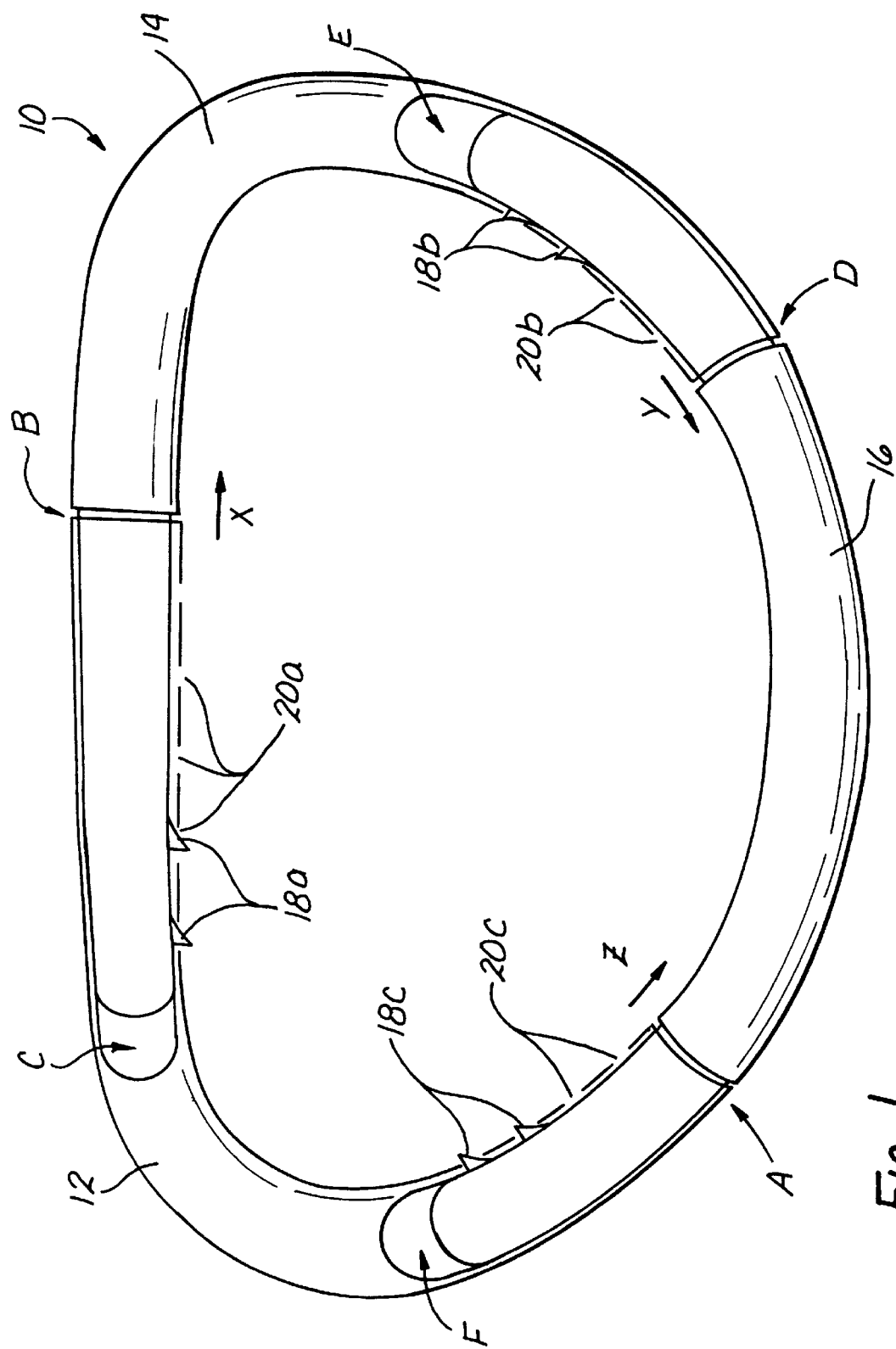
FIG. 1 is a partial perspective view of a first embodiment of the adjustable annuloplasty ring of the present invention.
Figure 2:
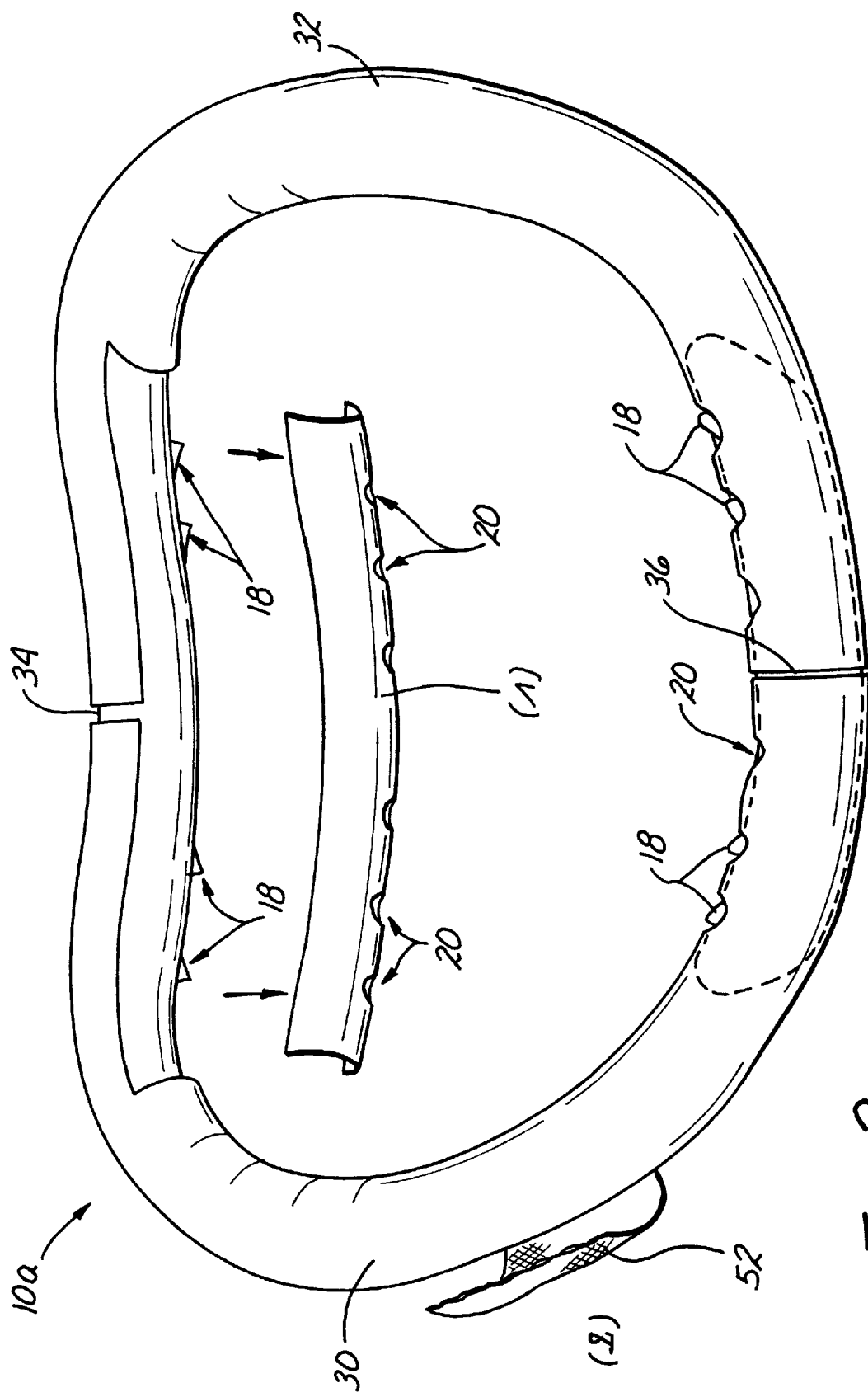
FIG. 2 is a partial cut-away perspective view of a second embodiment of the adjustable annuloplasty ring of the present invention.
Figure 3:
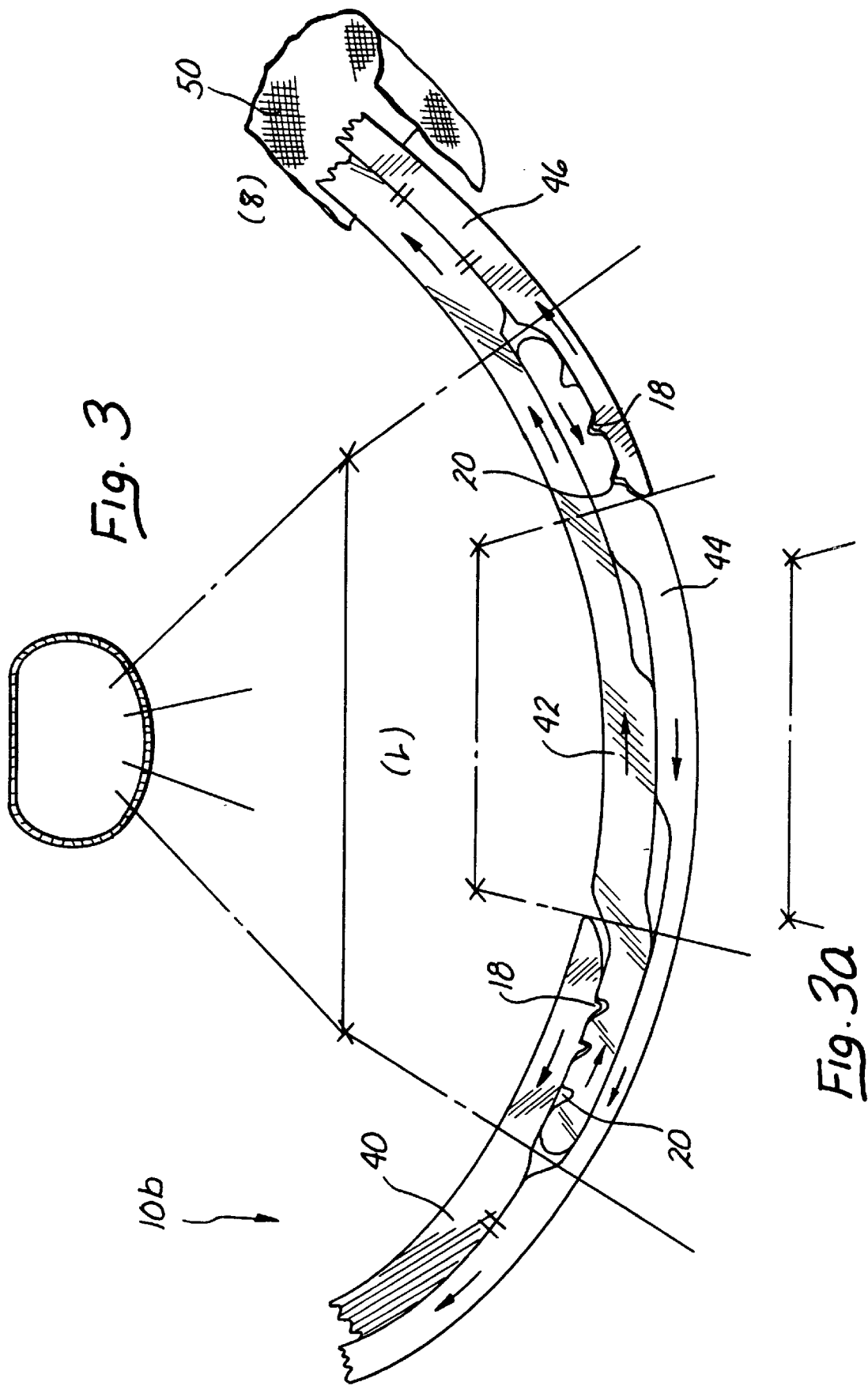
FIG. 3 is a reduced perspective view of a third embodiment of the adjustable annuloplasty ring of the present invention.

With reference to the drawings, FIGS. 1–3 show alternative ways of constructing the adjustable ring members 10, 10a and 10b of the present invention. The ring members 10, 10a and 10b shown in FIGS. 1–3 have a generally "D-shaped" configuration which corresponds to the normal anatomical shape of the mitral valve annulus. It will be appreciated that, if these ring members 10, 10a and 10b were intended for use in remodelling of the tricuspid valve, they would have the generally round configuration of the normal anatomical shape of the tricuspid valve annulus.

The ring member 10 shown in FIG. 1 comprises first 12, second 14 and third 16 tubular segments. Each segment 12, 14, 16 is joined to the two other segments to form a substantially unitary ring structure. The first segment 12 is tubular in configuration, having open ends A and B into which the corresponding ends of the second and third segments 14, 16 are inserted. The second segment 14 has a blunt tipped or closed first end C and an open tubular second end D. The third segment 16 has blunt tipped or closed first and second ends E and F, respectively.

The first end C of second segment 14 is inserted into the open second end B of the first segment 12. A series of raised lugs or teeth 18a protrude from one side of the portion of the second segment 14 which inserts into the second end B of the first segment 12. A corresponding series of apertures or detents 20a is formed in the side wall of the first segment 12. The individual teeth 18a snap into and frictionally engage the individual detents 20a, as shown.

Similarly, the first end E of the third segment 16 is inserted into the open second end D of the second segment 14. A series of raised lugs or teeth 18b protrude from one side of the portion of the third segment 16 which inserts into the second end D of the second segment 14. A corresponding series of apertures or detents 20b is formed in the side wall of the second segment 14. The individual teeth 18b snap into and frictionally engage the individual detents 20b, as shown.

Also, the second end F of the third segment 16 is inserted into the open first end A of the first segment 12. A series of raised lugs or teeth 18c protrude from one side of the portion of the third segment 16 which inserts into the first end A of the first segment 12. A corresponding series of apertures or detents 20c is formed in the sidewall of the first segment 12. The individual teeth 18c snap into and frictionally engage the individual detents 20c, as shown.

The individual teeth 18 are configured and constructed such that, when sufficient dilatory pressure is applied to the inner surface of the ring 10, the segments 12, 14, 16 will spread apart and the teeth 18 will be caused to move out of the detents 20 within which they are positioned and will slidably advance and snap into the next available detents in the series, thereby effecting one incremental increase in the annular size of the ring. Further application of additional dilatory pressure will cause the teeth 18 to move to the next available detents 20 in the series, thereby effecting a second incremental increase in size, and so on.

FIG. 2 shows an alternative ring 10a comprising first and second semi-annular tubular segments 30, 32 which are joined together in end to end fashion, as shown, to form the desired annular configuration of the ring 10a. Rack bars 34, 36 insert into the opposing open ends of the first and second tubular segments 30, 32. Teeth 18 protrude laterally from the portions of each rack bar 34, 36 which insert into the juxtaposed ends of the first and second semi-annular tubular segments 30, 32, as shown. Corresponding apertures or detents 20 are formed in the side walls of the tubular members 30, 32. The individual teeth 18 snap into and frictionally engage the individual detents 20, as shown. As described here above with respect to the embodiment shown in FIG. 1, the application of dilatory pressure against the inner surface of the ring 10a wyo cause the semi-annular tubular segments 30, 32 to move apart and the individual teeth 18 will advance to, and seat within, the next available detents 20, thereby causing the size of the ring 10a to increase by a predetermined incremental amount.

It will be appreciated that the components which make up the ring member 10 need not necessarily be of tubular configuration as shown in the embodiments of FIGS. 1 and 2. Indeed, as shown in FIG. 3, the ring member 10b may comprise of a plurality of non-tubular arcuate leaves 40, 42, 44, 46 assembled in overlapping relation to one another and contained within a distensible outer sheath 50, as shown.

In any embodiment of the invention, a suture ring 52, formed of material such as Dacron Mesh, is mounted about the periphery of the ring member 10, is mounted about the periphery of the ring member 10, 10a, 10b to facilitate suturing-in-place of the ring member 10, 10a, 10b to surrounding anatomical tissue.

Figure 4:
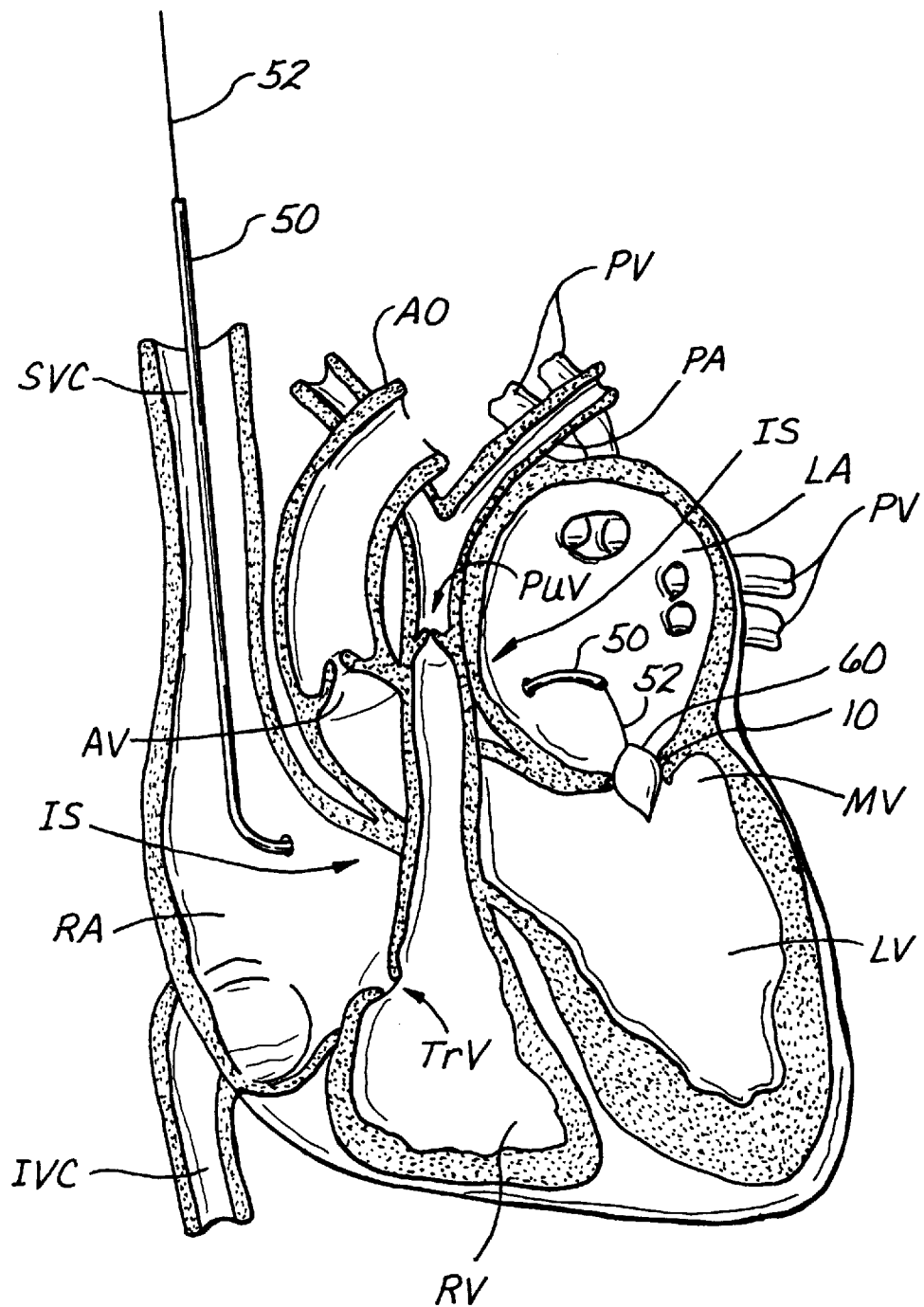
FIG. 4 is a cut-away illustration of a human heart having an adjustable annuloplasty ring of the present invention implanted at the mitral position, and showing the manner in which a dilation apparatus (e.g., a balloon catheter or expandable cage) may be advanced through a catheter, positioned transeptally, and utilized to effect in situ enlargement of the adjustable annuloplasty ring in accordance with the method of the present invention.

FIG. 4 shows a schematic illustration of the human heart having an adjustable annuloplasty ring 10 of the present invention implanted at the mitral position therein. The anatomical structures and major blood vessels of the heart are labeled, on FIG. 4, in accordance with the following legend:

| | |
|---|---|
| PV | Pulmonary Veins |
| PA | Pulmonary Artery |
| RPA | Right Pulmonary Artery |
| LPA | Left Pulmonary Artery |
| SVC | Superior Vena Cava |
| IVC | Inferior Vena Cava |
| AO | Aorta |
| RA | Right Atrium |
| RV | Right Ventricle |
| LA | Left Atrium |
| LV | Left Ventricle |
| IS | Interatrial Septum |
| AV | Aortic Valve Position |
| MV | Mitral Valve Position |
| TrV | Tricuspid Valve |
| PuV | Pulmonic Valve |

As shown in FIG. 4, one method by which the size of the annuloplasty ring 10 may be adjusted is through introduction of a guide catheter 50, via catheterization of the superior vena cava such that the distal end of the catheter is passed through the interatrial septum IS, using known septal penetration technique, and into the left atrium LA. A balloon dilation catheter 52, such as a valvuloplasty plasty catheter of the type commercially available, is then advanced through the lumen of the guide catheter 50, and positioned such that the balloon 60 of the balloon catheter 52 is within the annulus of the mitral valve MV. Thereafter, the balloon 60 is inflated, as shown, to cause the adjustable annuloplasty ring 10 to expand to a larger annular configuration.

In embodiments, such as those described and shown hereabove in FIGS. 1–3, it will be appreciated that the balloon 60 may be expanded to a specific diameter which will evoke a single incremental increase (i.e., from one notch to the next) of the mechanical expansion-controlling system of teeth and notches formed in the annuloplasty ring 10.

Similarly, when the annuloplasty ring 10 is implanted at the tricuspid valve TrV it will be desirable to advance the guide catheter 50 through the superior vena cava SVC to a point where the distal end of the guide catheter 50 is positioned within the right atrium RA of the heart. Thereafter, the balloon dilation catheter 52 may be advanced to a point where the distal portion of the balloon catheter 52 extends through the tricuspid valve TrV. Thereafter, the balloon 60 will be dilated so as to expand an annuloplasty ring of the present invention (not shown) when implanted within the tricuspid valve TrV.

It will be appreciated by those skilled in the art that various modifications additions and deletions may be made to the above-described embodiments, without departing from the intended spirit and scope of the invention. Accordingly, it is intended that all such modifications additions and deletions be included within the scope of the following claims.

What is claimed is:

1. A distensible annuloplasty ring for implantation in a heart valve annulus, comprising:

a plurality of biocompatible ring segments defining a periphery of the ring;

a first cooperating structure formed on at least one segment; and a second cooperating structure formed on another segment, the first and second cooperating structures engaging to prevent contraction of the ring and allow distension thereof.

2. The distensible annuloplasty ring of claim 1, wherein said cooperating structure comprises ratcheting structure for incremental distension.

3. The distensible annuloplasty ring of claim 1 wherein a first one of the segments comprises an open tubular end and a second one of the segments comprises a closed end, and wherein the first cooperating structure comprises a plurality of apertures provided in a spaced-apart manner at the open tubular end of the first segment, and the second cooperating structure comprises a plurality of teeth provided in a spaced-apart manner at the closed end of the second segment for insertion into some of the apertures.

4. The distensible annuloplasty ring of claim 3 wherein each of the plurality of teeth further comprises:

a slanted edge and a substantially vertical edge, wherein the slanted edge allows for the tooth to be slid from one aperture into an adjacent aperture to distend the ring, and wherein the substantially vertical edge prevents contraction of the ring.

5. The distensible annuloplasty ring of claim 1 wherein there are at least two first type of segments each comprising an open tubular end having a plurality of apertures provided in a spaced-apart manner, and at least one second type of segment comprising a bar having first and second ends that are insertable into the open tubular ends of the first type of segments, the bar comprising a plurality of teeth provided in a spaced-apart manner along the bar for insertion into some of the apertures of the first type of segments.

6. The distensible annuloplasty ring of claim 5 wherein each of the plurality of teeth further comprises:

a slanted edge and a substantially vertical edge, wherein the slanted edge allows for the tooth to be slid from one aperture into an adjacent aperture to distend the ring, and wherein the substantially vertical edge prevents the ring from contracting.

7. The distensible annuloplasty ring of claim 1 wherein the segments comprise:

a plurality of arcuate leaves movably coupled to one another by the first and second cooperating structure such that distention of the ring will cause the plurality of arcuate leaves to move apart from one another, thereby increasing the annular size of the ring.

8. The distensible annuloplasty ring of claim 2 wherein the plurality of arcuate leaves comprise a first leaf and a second leaf, the first and second leaves each comprising first and second ends, and wherein first cooperating structure comprises a plurality of apertures provided in a spaced-apart manner at the first end of the first leaf, and the second cooperating structure comprises a plurality of teeth provided in a spaced-apart manner at the second end of the second leaf for insertion into some of the apertures.

9. The distensible annuloplasty ring of claim 1 further comprising a saturable material disposed on said ring to facilitate suturing-in-place of said ring to surrounding anatomical tissue.

10. The distensible annuloplasty ring of claim 9 wherein said saturable material comprises a fabric mesh.

11. The distensible annuloplasty ring of claim 1 further comprising:

a substantially impermeable sheath positioned around said ring to prevent blood from contacting said ring.

12. A method of surgically supporting the annulus of a heart over an extended period, comprising:

implanting within the annulus a distensible annuloplasty ring having a plurality of biocompatible ring segments defining a periphery of the ring having a first size, wherein a first cooperating structure is formed on at least one segment, and a second cooperating structure is formed on another segment, the first and second cooperating structures engaging to prevent contraction of the ring and allow distension thereof, and subsequently, after a predetermined growth of the annulus, inserting a dilation apparatus into the ring and distending the annuloplasty ring to a size larger than the first size.

13. The method of claim 12, wherein said dilation apparatus comprises a balloon catheter.

* * * * *